US010493229B2

(12) United States Patent
Sun

(10) Patent No.: US 10,493,229 B2
(45) Date of Patent: Dec. 3, 2019

(54) BREATHING ASSISTANCE APPARATUS WITH LIQUID CONTAINMENT

(71) Applicant: Fisher & Paykel Healthcare Limited, Auckland (NZ)

(72) Inventor: Yi-Cheng Sun, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 523 days.

(21) Appl. No.: 15/113,787

(22) PCT Filed: Jan. 29, 2015

(86) PCT No.: PCT/NZ2015/050005
§ 371 (c)(1),
(2) Date: Jul. 22, 2016

(87) PCT Pub. No.: WO2015/115916
PCT Pub. Date: Aug. 6, 2015

(65) Prior Publication Data
US 2016/0375216 A1 Dec. 29, 2016

Related U.S. Application Data

(60) Provisional application No. 61/933,775, filed on Jan. 30, 2014.

(51) Int. Cl.
*A61M 16/00* (2006.01)
*A61M 16/08* (2006.01)
(Continued)

(52) U.S. Cl.
CPC ........ *A61M 16/16* (2013.01); *A61M 16/0066* (2013.01); *A61M 16/0875* (2013.01); *A61M 16/109* (2014.02); *A61M 2205/21* (2013.01)

(58) Field of Classification Search
CPC ............... A61M 16/16; A61M 16/109; A61M 2205/21; A61M 16/161; A61M 16/162;
(Continued)

(56) References Cited

U.S. PATENT DOCUMENTS

| 6,935,337 B2 * | 8/2005 | Virr ....................... A61M 16/16 128/203.16 |
| 2007/0230927 A1 * | 10/2007 | Kramer ................ A61M 16/16 392/403 |

FOREIGN PATENT DOCUMENTS

| AU | 3253100 | 11/2000 |
| JP | 2000-337670 | 12/2000 |

(Continued)

OTHER PUBLICATIONS

GB Examination Report; GB1612153 dated Nov. 1, 2017; 3 pages.
(Continued)

*Primary Examiner* — Jan Christopher L Merene
*Assistant Examiner* — Cana A Gallegos
(74) *Attorney, Agent, or Firm* — Knobbe, Martens, Olson & Bear, LLP

(57) ABSTRACT

A breathing assistance apparatus has a main body. A humidification compartment is defined within the main body and is adapted to receive a humidification chamber. A flow generator is positioned within the main body. The flow generator and the humidification compartment are fluidly connected and a liquid containment compartment is interposed between the flow generator and the humidification compartment. The liquid containment compartment is fluidly connected to both the flow generator and the humidification compartment.

26 Claims, 7 Drawing Sheets

(51) Int. Cl.
*A61M 16/10* (2006.01)
*A61M 16/16* (2006.01)

(58) Field of Classification Search
CPC .............. A61M 16/164; A61M 16/165; A61M 16/167; A61M 16/168; F24F 6/00
See application file for complete search history.

(56) References Cited

FOREIGN PATENT DOCUMENTS

| | | |
|---|---|---|
| JP | 2004-524087 | 8/2004 |
| WO | WO02/066106 | 8/2002 |
| WO | WO 2002/066106 A1 | 8/2002 |
| WO | WO 2005/018724 | 3/2005 |
| WO | WO 2007/019625 A1 | 2/2007 |
| WO | WO 2008/024001 | 2/2008 |
| WO | WO 2009/156921 A1 | 12/2009 |
| WO | WO 2013/135318 | 9/2013 |

OTHER PUBLICATIONS

European Search Report; PCT/NZ2015/050005; dated Sep. 26, 2017; 12 pages.
International Search Report; PCT/NZ2015/050005; dated Apr. 27, 2015; 4 pages.
AU Examination Report; 2015211502 dated Dec. 20, 2018; 4 pages.
JP Examination report for JP 2016-549441 dated Oct. 18, 2019.
Examination Report for Australian Application No. 2015211502 dated Jul. 15, 2019 in 2 pages.

* cited by examiner

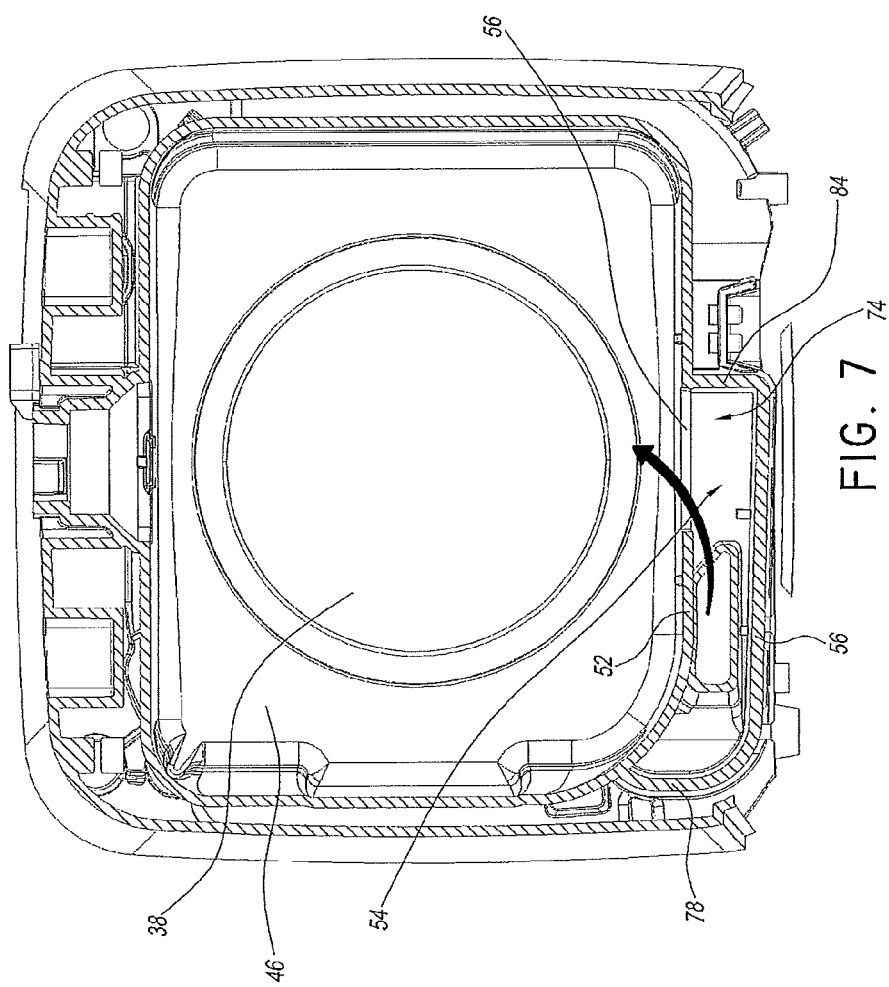

BREATHING ASSISTANCE APPARATUS WITH LIQUID CONTAINMENT

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention generally relates to respiratory devices. More particularly, the present invention relates to respiratory devices receiving pressurized breathing gases for humidification and having liquid isolation constructions.

Description of the Related Art

Breathing treatment devices typically include an airflow generator to supply pressurized gases. In some breathing treatment devices the device may include an integrated water supply chamber. The water chamber can include a supply of water that is used to humidify the breathing gases that are being supplied by the breathing treatment device.

In some configurations the breathing treatment devices are designed to be portable and/or movable. When such devices are moved while containing a water supply reservoir, the reservoir may tip and allow water to spill from the water reservoir into other regions of the breathing treatment devices.

SUMMARY OF THE INVENTION

To protect various components, it would be desirable if the spilled water or other liquids could be contained and the infiltration of the water or liquid could be controlled. Accordingly, certain features, aspects and advantages of the present invention relate to providing a liquid containment construction. It also is an object of the present invention to at least provide the industry and users with a useful choice.

The invention broadly consists in a breathing assistance apparatus comprising a main body, a humidification compartment defined within the main body and adapted to receive a humidification chamber, a flow generator positioned within the main body, the flow generator and the humidification compartment being fluidly connected and a liquid containment compartment being interposed within the main body between the flow generator and the humidification compartment, the liquid containment compartment being fluidly connected to both the flow generator and the humidification compartment such that a gas flow path from the flow generator to the humidification compartment passes through the liquid containment compartment, and wherein the liquid containment compartment comprises a first opening that defines an outlet for gases flow out of the liquid containment compartment to the humidification compartment and a second opening that defines an inlet for gases flow into the liquid containment compartment from the flow generator, the first opening and the second opening of the liquid containment compartment being offset from each other in at least two orthogonal spatial directions.

In some configurations, the first opening and the second opening of the liquid containment compartment are offset horizontally and vertically.

In some configurations, the first opening and the second opening of the liquid containment compartment are offset from each other in three orthogonal spatial directions. In one example, the first opening and the second opening of the liquid containment compartment may be offset horizontally in two orthogonal directions and vertically.

In some configurations, no portion of the first opening is vertically aligned with the second opening.

In some configurations, no portion of the first opening is horizontally aligned with the second opening.

In some configurations, the liquid containment compartment comprises a lower surface and the second opening being positioned generally vertically higher than the lower surface. In one example, the second opening spans a vertical distance and the lowermost portion of the second opening is vertically higher than the lower surface of the liquid containment compartment. In another example, the lower surface of the liquid containment compartment spans a vertical distance and the second opening is vertically higher than any portion of the lower surface that is directly adjacent to the second opening.

In some configurations, the second opening is canted toward the first opening.

In some configurations, a lowermost portion of the second opening is vertically higher than a lowermost portion of the lower surface of the liquid containment compartment.

In some configurations, the second opening has a lip defined on a portion of the second opening that is on an opposite side of the second opening from the first opening. In one example, the lip overhangs a passage defined within a pedestal leading to the second opening, the passage forming part of the gas flow path.

In some configurations, the second opening has a narrowing region defined on a portion of the second opening that is disposed closest to the first opening.

In some configurations, the second opening is provided atop of a pedestal extending within the liquid containment compartment from the lower surface of the liquid containment compartment, the pedestal comprising a passage fluidly connected to the flow generator to form part of the gas flow path.

In some configurations, the second opening is fluidly connected to the flow generator by one or more passages within the main body that form part of the gas flow path.

In some configurations, the main body comprises an upper housing and a lower housing that are configured to be secured together, and wherein the liquid containment compartment comprises a lower surface that is part of the lower housing of the main body and a vertical wall defining the sides of the liquid containment compartment that is part of the upper housing of the main body.

In some configurations, a portion of the vertical wall of the liquid containment compartment corresponds to a portion of a vertical wall that defines the humidification compartment. In one example, the first opening extends through the portion of the vertical wall of the liquid containment compartment that corresponds to the vertical wall of the humidification compartment.

In some configurations, a portion of the vertical wall of the liquid containment compartment corresponds to a portion of an outer wall of the main body provided by the upper housing.

In some configurations, the liquid containment compartment comprises a ridge that defines the periphery of the lower surface of the liquid containment compartment and which extends from the lower housing of the main body, the ridge matching the configuration of the vertical wall of the liquid containment compartment provided in the upper housing such that the ridge of the lower housing and vertical wall of the upper housing abut each other to form the liquid containment compartment when the main body is assembled.

In some configurations, the ridge of the liquid containment compartment defines and encircles a reservoir of the liquid containment compartment.

In some configurations, the ridge of the liquid containment compartment surrounds the second opening.

In some configurations, a seal is provided between ridge of the lower housing and the vertical wall of the upper housing that form the liquid containment compartment. In one example, the ridge comprises a groove and the seal is provided within the groove.

In some configurations, the flow generator is mounted to or within the lower housing of the main body.

Other aspects are also described in the following. In some configurations, a breathing assistance apparatus comprises a main body. A humidification compartment is defined within the main body and is adapted to receive a humidification chamber. A flow generator is positioned within the main body. The flow generator and the humidification compartment are fluidly connected and a liquid containment compartment is interposed between the flow generator and the humidification compartment. The liquid containment compartment is fluidly connected to both the flow generator and the humidification compartment.

In some such configurations, a gas flow path from the flow generator to the humidification compartment passes through the liquid containment compartment.

In some such configurations, the liquid containment compartment comprises a first opening that defines an outlet for gases flow out of the liquid containment compartment and a second opening that defines an inlet for gases flow into the liquid containment compartment. The liquid containment compartment comprises a lower surface and the second opening is positioned generally vertically higher than the lower surface.

In some such configurations, the second opening is canted toward the first opening.

In some such configurations, a lowermost portion of the second opening is vertically higher than a lowermost portion of the lower surface.

In some such configurations, the second opening has a lip defined on a portion of the second opening that is on an opposite side of the second opening from the first opening.

In some such configurations, the lip overhangs a passage defined within a pedestal leading to the second opening.

In some such configurations, the liquid containment compartment comprises a first opening that defines an outlet for gases flow out of the liquid containment compartment and a second opening that defines an inlet for gases flow into the liquid containment compartment. The first opening is offset from the second opening such that the first opening is not vertically aligned with the second opening.

In some such configurations, no portion of the first opening is vertically aligned with the second opening.

In some such configurations, the first opening and the second opening are offset from each other in three orthogonal spatial directions.

The term "comprising" as used in the specification and claims means "consisting at least in part of". When interpreting a statement in this specification and claims that includes "comprising", features other than that or those prefaced by the term may also be present. Related terms such as "comprise" and "comprises" are to be interpreted in the same manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

BRIEF DESCRIPTION OF THE DRAWINGS

These and other features, aspects and advantages of the present invention will now be described with reference to the drawings of a preferred embodiment, which embodiment is intended to illustrate and not to limit the invention, and in which figures:

FIG. 7 is a section view illustrating airflow path through the liquid isolation chamber of the respiratory humidification device of FIG. 1.

DETAILED DESCRIPTION OF THE PREFERRED EMBODIMENT

Figure 1:
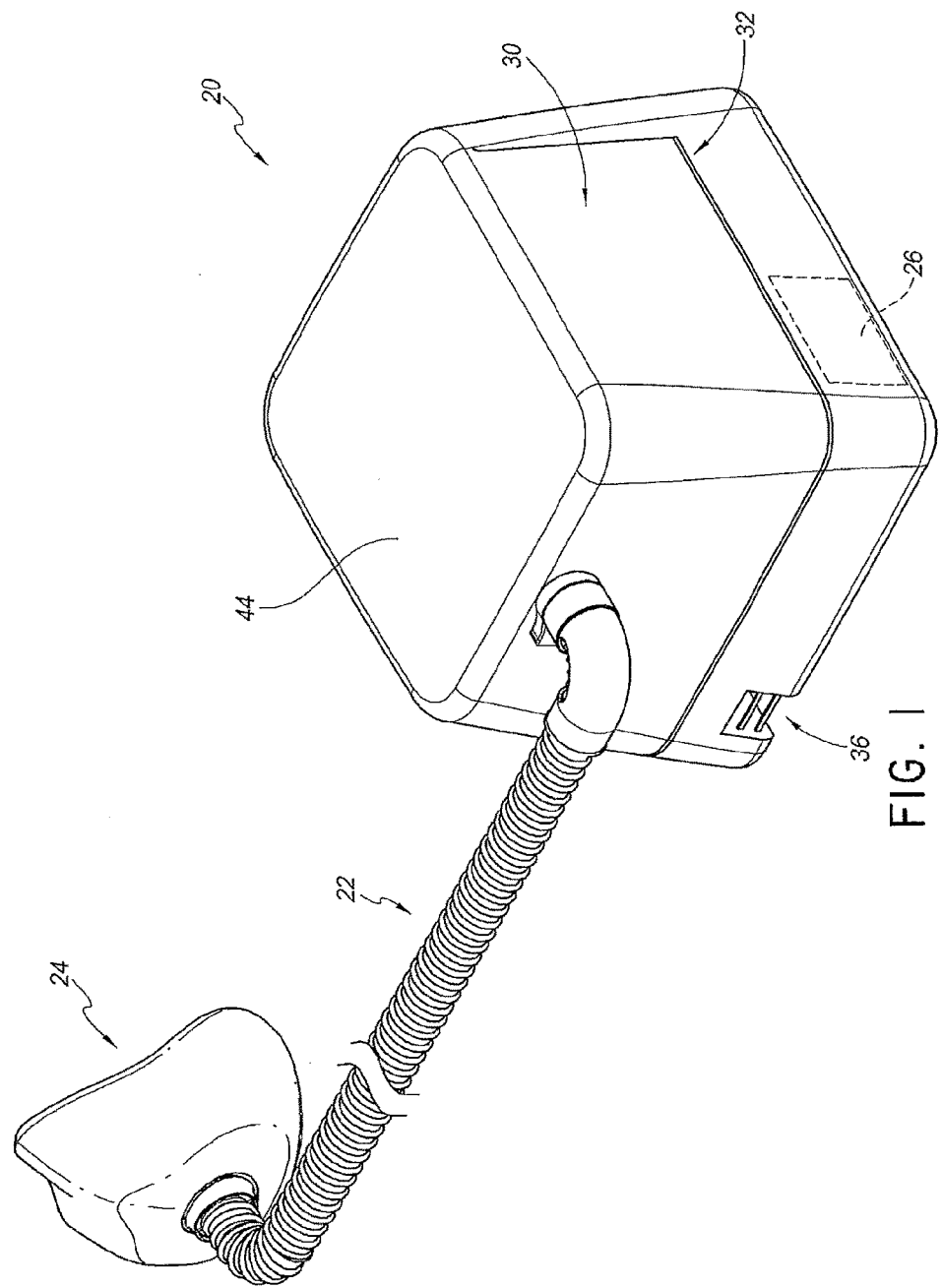
FIG. 1 is a perspective view of a system including a respiratory humidification device that is arranged and configured in accordance with certain features aspects and advantages of the present invention.

With reference now to FIG. 1, a breathing assistance apparatus 20 is shown that is arranged and configured in accordance with certain features, aspects and advantages of the present invention. In the illustrated configuration, the breathing assistance apparatus 20 is connected to a conduit 22 and the conduit 22 is connected to a user interface 24, such as a breathing mask or the like. Any suitable user interface 24 can be used.

The breathing assistance apparatus 20 is configured to deliver a flow of pressurized breathing gases to the user through the conduit 22 and the user interface 24. Accordingly, the illustrated breathing assistance apparatus 20 comprises a flow generator 26, which has been schematically illustrated in FIG. 1. The flow generator 26 can have any suitable construction. In some configurations, the flow generator 26 is a blower that draws ambient air into the breathing assistance apparatus 20 and generates the flow of pressurized breathing gases.

Figure 2:
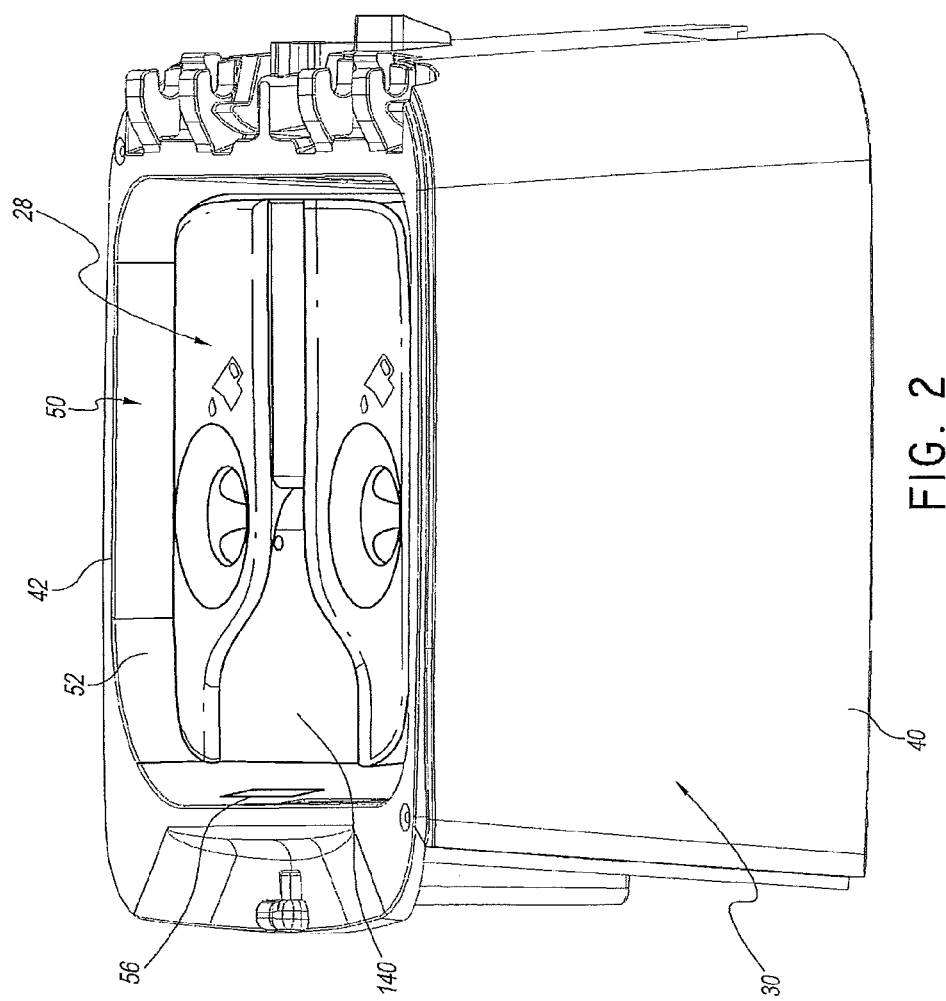
FIG. 2 is a perspective view of the respiratory humidification device of FIG. 1.

The breathing assistance apparatus 20 also is configured to humidify the flow of pressurized breathing gases prior to deliver to the user. Accordingly, as illustrated in FIG. 2, the illustrated breathing assistance apparatus 20 also comprises a humidification chamber 28. The humidification chamber 28 can be removable from the breathing assistance apparatus 20. Any suitable construction can be used for the humidification chamber 28. The humidification chamber 28 can be configured to contain a volume of liquid, such as water. The flow of pressurized breathing gases can pass over the volume of liquid en route to the user such that the flow of pressurized breathing gases can increase in humidity.

Figure 4:
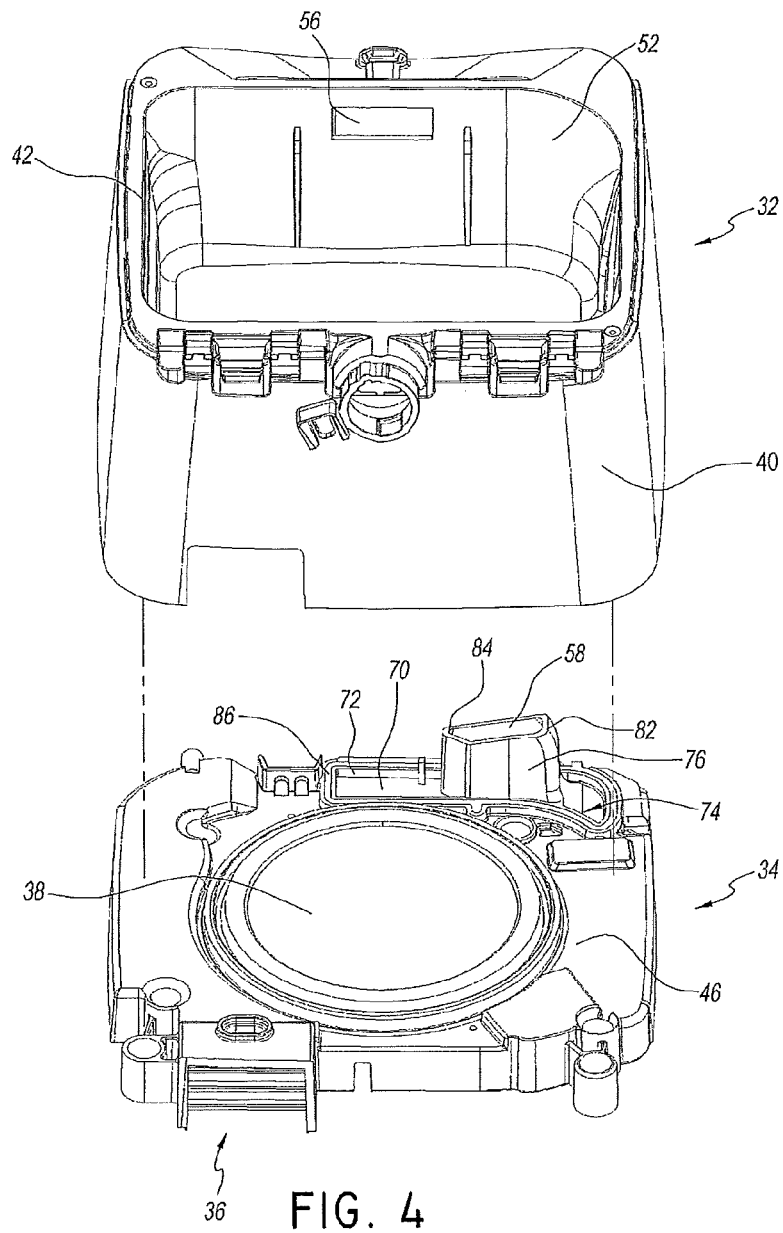
FIG. 4 is an exploded perspective view of a portion of the respiratory humidification device of FIG. 1.

As illustrated, the breathing assistance apparatus 20 generally comprises a main body 30. With reference to FIG. 4, the main body 30 can comprise an upper housing 32 and a lower housing 34. The upper housing 32 and the lower housing 34 can be secured together in any suitable manner. In some configurations, the bottom of the lower housing 34 can be enclosed by a further cover.

With continued reference to FIG. 4, the lower housing 34 can include an air inlet 36 through which the flow generator 26 draws air. The flow generator 26 can be mounted to or within the lower housing 34. The lower housing 34 also can support a heating element 38. The liquid within the humidification chamber 28 can be heated through an interaction with the heating element 38. In some configurations, the heating element 38 can be a heater plate and the humidification chamber 28 can rest on the heater plate. Other configurations are possible.

With reference to FIG. 2, the main body 30 comprises at least one outer wall 40. In the illustrated configuration, the main body 30 comprises four generally vertical outer walls 40. An upper portion of the at least one outer wall 40 generally defines an opening 42. As shown in FIG. 1, the opening 42 can be closed with a lid 44. The lid 44 can seal the opening 42 in some configurations.

The main body 30 contains a humidification compartment 50 that receives the humidification chamber 28. In the illustrated configuration, the humidification compartment 50 is generally defined within the at least one outer wall 40, the lid 44 and a base surface 46. More particularly, in the illustrated configuration, at least one generally vertical inner wall 52 defines at least a portion of the humidification compartment 50. Even more particularly, four generally vertical walls, including the at least one generally vertical inner wall 52, largely define the humidification compartment 50.

A liquid containment compartment 54 can be separated from the humidification compartment 50. In some configurations, the liquid containment compartment 54 limits the travel of liquid that may spill from the humidification chamber 28. In some configurations, the liquid containment compartment 54 can limit the travel of liquid that may be spilled within the humidification compartment 50 and outside of the humidification chamber 28.

The liquid containment compartment 54 can be positioned within the main body 30 of the breathing assistance apparatus 20. In the illustrated configuration, the liquid containment compartment 54 is integrated into the main body 30 of the breathing assistance apparatus 20. The liquid containment compartment 54 and the flow generator 26 both can be integrated into the main body 30. In some configurations, the liquid containment compartment 54 is fluidly connected to the flow generator 26 and to the humidification compartment 50. In some such configurations, the liquid containment compartment 54 is positioned between the flow generator 26 and the humidification compartment 54. In some configurations, the liquid containment compartment 54 can be positioned between the outer wall 40 and the inner wall 52 of the main body. In some configurations, the inner wall 52 separates the humidification compartment 50 from the liquid containment compartment 54.

Figure 3:
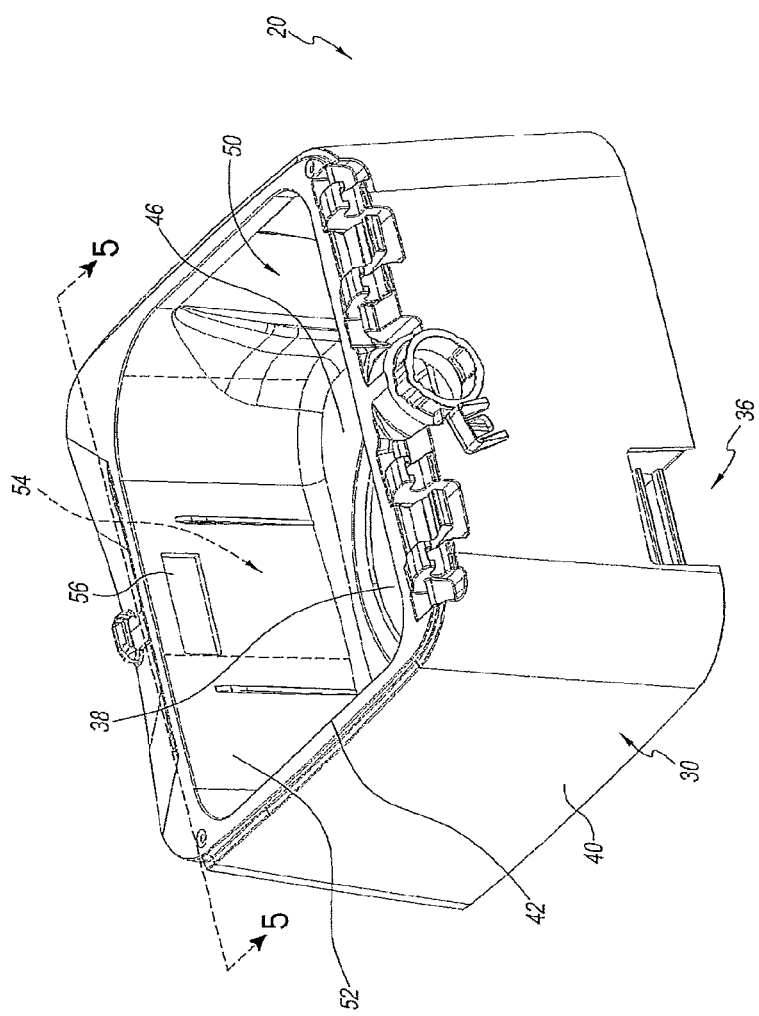
FIG. 3 is a perspective view of a portion of the respiratory humidification device of FIG. 1.

The liquid containment compartment 54 can include two openings. A first opening 56, as shown in FIG. 3, extends through the inner wall 52. The first opening 56 defines a gas inlet for the humidification compartment 50 and a gas outlet for the liquid containment compartment 54. Gases flowing through the first opening 56 will be received by the humidification chamber 28 and will be humidified prior to delivery to the user. In other words, with the lid 44 in position and closed, the humidification chamber 28 is sealed in position within the humidification compartment 50. Gas passing through the first opening 56 will flow into the humidification compartment 50, and from the humidification compartment, the gases will flow into the humidification chamber 28 prior to passing out of the breathing assistance apparatus 20.

Figure 5:
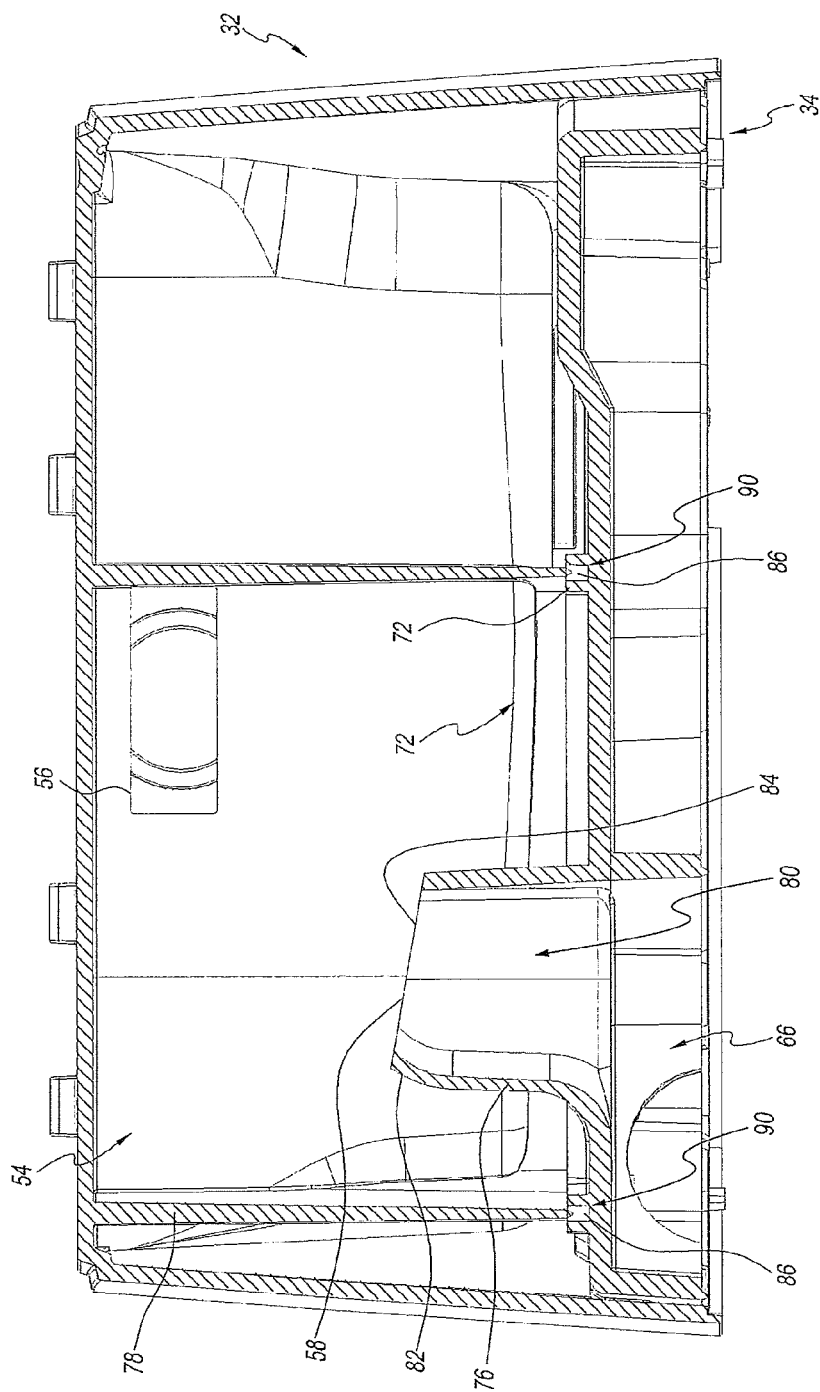
FIG. 5 is a section view of a portion of the humidification device of FIG. 1 taken along the line 5-5 in FIG. 3.

A second opening 58, shown in FIG. 4, defines a gas inlet into the liquid containment compartment 54 and a gas outlet for flow from a passage 66 leading from the flow generator 26. In one configuration, the first opening 56 is in the upper housing 32 and the second opening 58 is in the lower housing 34. In some configurations, the first opening 56 is offset both horizontally and vertically from the second opening. In some configurations, the first opening 56 is offset at least horizontally from the second opening 58, as shown in FIG. 5 (i.e., the first opening 56 is to the right of the second opening 58). In some configurations, the first opening 56 is completely offset at least horizontally from the second opening 58. In some configurations, the two openings 56, 58 are offset in two orthogonal directions (e.g., horizontally and vertically). In some configurations, the two openings 56, 58 are offset in three orthogonal directions (horizontally in two orthogonal directions and vertically). Offset positioning of the first opening 56 relative to the second opening 58 reduces the likelihood of liquids spilling, draining, depositing or otherwise passing through the first opening 56 into the liquid containment compartment 54 passing further upstream toward the flow generator 26 relative to the liquid containment chamber 54. In other words, liquid is unlikely to easily pass through the first opening 56 and into the second opening 58. As such, liquid infiltration from the humidification chamber 28 toward the flow generator 26 can be inhibited.

Figure 6:
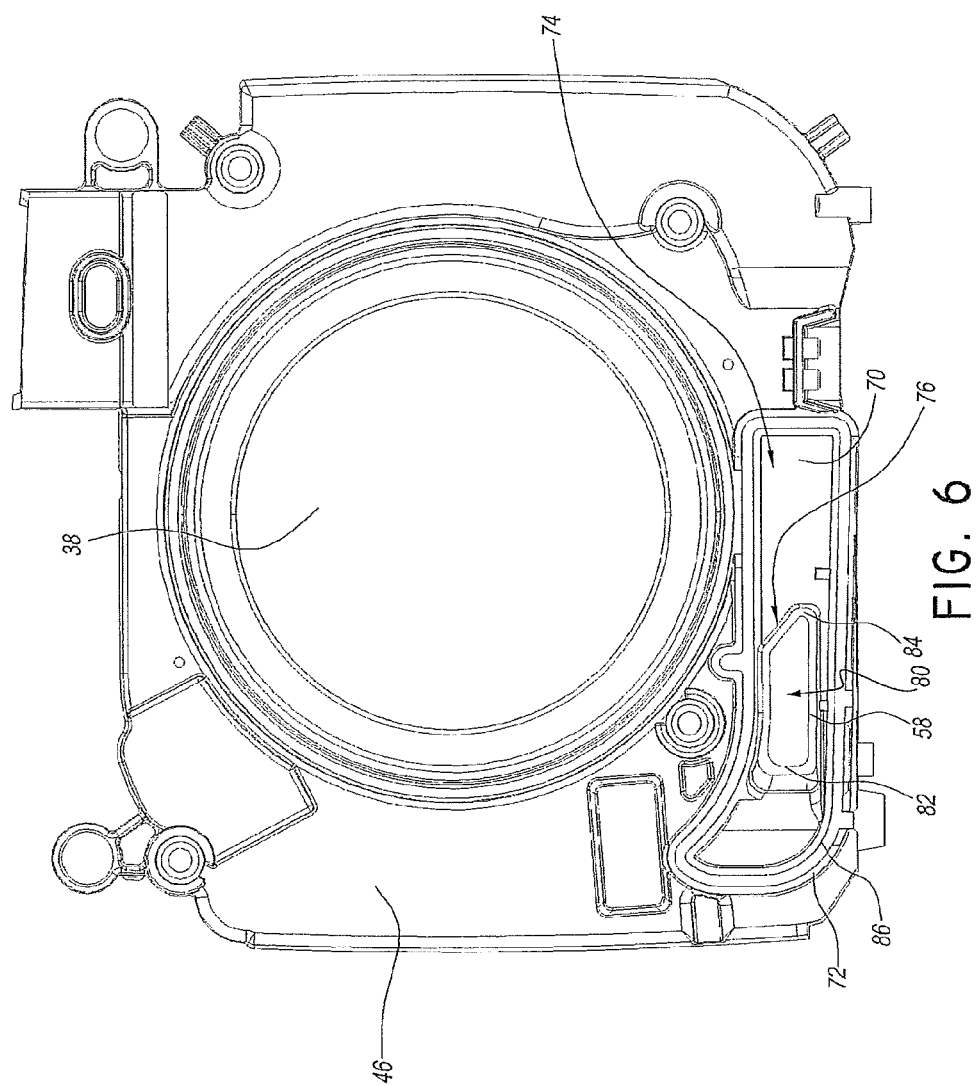
FIG. 6 is top view of a lower portion of the respiratory humidification device of FIG. 1.

With reference to now to FIG. 4, the liquid containment compartment 54 comprises at least a lower surface 70. The lower surface 70 can be formed as part of the lower housing 34. In the illustrated configuration, a ridge 72 can be defined on a portion of the lower housing 34. The illustrated ridge 72 can generally encircle a reservoir 74. As shown in FIG. 6, the ridge 72 generally surrounds the second opening 58. Other configurations are possible.

With reference again to FIG. 5, the second opening 58 is vertically higher than the lower surface 70. In some configurations, the second opening 58 spans a vertical distance and the lowermost portion of the second opening 58 is vertically higher than the lower surface 70. In some configurations, the lower surface 70 can span a vertical distance (i.e., not be substantially flat) and the second opening 58 is vertically higher than any portion of the lower surface 70 that is directly adjacent to the second opening 58.

In the illustrated configuration, the second opening 58 is formed atop of a pedestal 76. The pedestal 76 can be integrally formed with the lower housing 34. The pedestal 76 generally encircles a passage 80 as shown in FIGS. 5 and 6. At the upper end of the illustrated pedestal 76, the second opening 58 is generally canted such that the upper surface of the illustrated pedestal angles toward the first opening 56. Moreover, with reference to FIG. 5, at least an inner surface of the pedestal 76 that is furthest from the first opening 56 bends toward the first opening 56. The deflected portion of pedestal 76 that is generally adjacent the second opening 58 forms a lip 82. The lip 82 can help to deflect the gases flow toward the general direction of the first opening 56.

With reference to FIG. 6, the second opening 58 also has a narrowing region 84. The narrowing region 84 is disposed closest to the first opening 56 in the illustrated configuration. As shown in FIG. 5, the narrowing region 84 does not extend upward to the same extent as the lip region 82. The lip region 82 and/or the narrowing region 84 can help tailor and direct the gas flow in a desired manner. Other configurations are possible.

As described above, in some configurations, at least a portion of the liquid containment compartment 54 is defined between the inner wall 52 and the outer wall 40 of the main body 30. With reference to FIG. 7, at least a first wall 78 and, in some configurations, a second wall 84 can cooperate with the inner wall 52 and the outer wall 40 to define the sides of the liquid containment compartment 54. These walls 40, 52, 78, 84 can be integrally formed with the upper housing 32.

The ridge 72 can match the configuration of these walls 40, 52, 78, 84. As such, the ridge 72 and these walls 40, 52, 78 and 84 can abut each other. To reduce the likelihood of leaks at the junction of the ridge 72 and the walls 40, 52, 78, 84, a seal 86 can be positioned between the upper housing 32 and the lower housing 34. In the illustrated configuration, the seal 86 is positioned within a groove 90 (see FIG. 5). The groove 90 may be positioned within the ridge 72. The seal 86 can be formed of a more resilient material than the ridge 72. As such, the seal 86 can deform upon contact with the walls 40, 52, 78, 84. The compression of the seal 86 can reduce the likelihood of liquid or gas leaks into or out of the liquid containment compartment 54.

Moreover, in the event of liquid passing through the first opening 56 into the liquid containment chamber 54, the liquid will be held within the liquid containment chamber 54. As such, the seal 86 between the upper housing 32 and the lower housing 34 can reduce the likelihood of liquid migration even if the level of liquid within the liquid containment chamber 54 exceeds the height of the ridge 72.

Although the present invention has been described in terms of a certain embodiment, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

The invention claimed is:

1. A breathing assistance apparatus comprising a main body, a humidification compartment defined within the main body and adapted to receive a humidification chamber, a flow generator positioned within the main body, the flow generator and the humidification compartment being fluidly connected and a liquid containment compartment being interposed within the main body between the flow generator and the humidification compartment, the liquid containment compartment being fluidly connected to both the flow generator and the humidification compartment such that a gas flow path from the flow generator to the humidification compartment passes through the liquid containment compartment, and wherein the liquid containment compartment comprises:
a first opening that defines an outlet for gases flow out of the liquid containment compartment to the humidification compartment;
a second opening that defines an inlet for gases flow into the liquid containment compartment from the flow generator, the first opening and the second opening of the liquid containment compartment being offset from each other in at least two orthogonal spatial directions; and
a lower surface, wherein the second opening is positioned generally vertically higher than the lower surface and the second opening is provided atop of a pedestal extending within the liquid containment compartment from the lower surface of the liquid containment compartment, the pedestal comprising a passage fluidly connected to the flow generator to form part of the gas flow path.

2. The breathing assistance apparatus according to claim 1 wherein the first opening and the second opening of the liquid containment compartment are offset horizontally and vertically.

3. The breathing assistance apparatus according to claim 1 wherein the first opening and the second opening of the liquid containment compartment are offset from each other in three orthogonal spatial directions.

4. The breathing assistance apparatus according to claim 3 wherein the first opening and the second opening of the liquid containment compartment are offset horizontally in two orthogonal directions and vertically.

5. The breathing assistance apparatus according to claim 1 wherein no portion of the first opening is vertically aligned with the second opening.

6. The breathing assistance apparatus according to claim 1 wherein no portion of the first opening is horizontally aligned with the second opening.

7. The breathing assistance apparatus according to claim 1 wherein the second opening spans a vertical distance and the lowermost portion of the second opening is vertically higher than the lower surface of the liquid containment compartment.

8. The breathing assistance apparatus according to claim 1 wherein the lower surface of the liquid containment compartment spans a vertical distance and the second opening is vertically higher than any portion of the lower surface that is directly adjacent to the second opening.

9. The breathing assistance apparatus according to claim 1 wherein the second opening is canted toward the first opening.

10. The breathing assistance apparatus according to claim 1 wherein a lowermost portion of the second opening is vertically higher than a lowermost portion of the lower surface of the liquid containment compartment.

11. The breathing assistance apparatus according to claim 1 wherein the second opening has a lip defined on a portion of the second opening that is on an opposite side of the second opening from the first opening.

12. The breathing assistance apparatus according to claim 11 wherein the lip overhangs a passage defined within a pedestal leading to the second opening, the passage forming part of the gas flow path.

13. The breathing assistance apparatus according to claim 1 wherein the second opening has a narrowing region defined on a portion of the second opening that is disposed closest to the first opening.

14. The breathing assistance apparatus according to claim 1 wherein the second opening is fluidly connected to the flow generator by one or more passages within the main body that form part of the gas flow path.

15. The breathing assistance apparatus according to claim 1 wherein the main body comprises an upper housing and a lower housing that are configured to be secured together, and wherein the lower surface of the liquid containment compartment is part of the lower housing of the main body and wherein the liquid containment compartment comprises a vertical wall defining the sides of the liquid containment compartment that is part of the upper housing of the main body.

16. The breathing assistance apparatus according to claim 15 wherein a portion of the vertical wall of the liquid containment compartment corresponds to a portion of a vertical wall that defines the humidification compartment.

17. The breathing assistance apparatus according to claim 16 wherein the first opening extends through the portion of the vertical wall of the liquid containment compartment that corresponds to the vertical wall of the humidification compartment.

18. The breathing assistance apparatus according to claim 15 wherein a portion of the vertical wall of the liquid containment compartment corresponds to a portion of an outer wall of the main body provided by the upper housing.

19. The breathing assistance apparatus according to claim 15 wherein the liquid containment compartment comprises a ridge that defines the periphery of the lower surface of the liquid containment compartment and which extends from the lower housing of the main body, the ridge matching the configuration of the vertical wall of the liquid containment compartment provided in the upper housing such that the ridge of the lower housing and vertical wall of the upper housing abut each other to form the liquid containment compartment when the main body is assembled.

20. The breathing assistance apparatus according to claim 19 wherein the ridge of the liquid containment compartment defines and encircles a reservoir of the liquid containment compartment.

21. The breathing assistance apparatus according to claim 19 wherein the ridge of the liquid containment compartment surrounds the second opening.

22. The breathing assistance apparatus according to claim 19 wherein a seal is provided between ridge of the lower housing and the vertical wall of the upper housing that form the liquid containment compartment.

23. The breathing assistance apparatus according to claim 22 wherein the ridge comprises a groove and the seal is provided within the groove.

24. The breathing assistance apparatus according to claim 15 wherein the flow generator is mounted to or within the lower housing of the main body.

25. The breathing assistance apparatus according to claim 1 wherein the first opening is positioned vertically higher than the second opening.

26. A breathing assistance apparatus comprising a main body, a humidification compartment defined within the main body and adapted to receive a humidification chamber, a flow generator positioned within the main body, the flow generator and the humidification compartment being fluidly connected and a liquid containment compartment being interposed within the main body between the flow generator and the humidification compartment, the liquid containment compartment being fluidly connected to both the flow generator and the humidification compartment such that a gas flow path from the flow generator to the humidification compartment passes through the liquid containment compartment, and wherein the liquid containment compartment comprises a first opening that defines an outlet for gases flow out of the liquid containment compartment to the humidification compartment and a second opening that defines an inlet for gases flow into the liquid containment compartment from the flow generator, the first opening and the second opening of the liquid containment compartment being offset from each other in at least two orthogonal spatial directions, wherein the main body comprises an upper housing and a lower housing that are configured to be secured together, and wherein the liquid containment compartment comprises a lower surface that is part of the lower housing of the main body and a vertical wall defining the sides of the liquid containment compartment that is part of the upper housing of the main body, wherein a portion of the vertical wall of the liquid containment compartment corresponds to a portion of a vertical wall that defines the humidification compartment, wherein the first opening extends through the portion of the vertical wall of the liquid containment compartment that corresponds to the vertical wall of the humidification compartment.

* * * * *